United States Patent
Wander et al.

(10) Patent No.: US 10,004,847 B2
(45) Date of Patent: Jun. 26, 2018

(54) OCCLUSION DETECTION

(71) Applicant: SMITHS MEDICAL ASD, INC., Rockland, MA (US)

(72) Inventors: Jacob A. Wander, New Brighton, MN (US); Grant A. Adams, Coon Rapids, MN (US); Christopher A. Lacy, Arden Hills, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 124 days.

(21) Appl. No.: 14/400,509

(22) PCT Filed: May 23, 2013

(86) PCT No.: PCT/US2013/042388
§ 371 (c)(1),
(2) Date: Nov. 11, 2014

(87) PCT Pub. No.: WO2013/177379
PCT Pub. Date: Nov. 28, 2013

(65) Prior Publication Data
US 2015/0133890 A1    May 14, 2015

Related U.S. Application Data

(60) Provisional application No. 61/651,860, filed on May 25, 2012.

(51) Int. Cl.
*A61M 5/168*    (2006.01)
*A61M 5/145*    (2006.01)
*A61B 5/00*    (2006.01)

(52) U.S. Cl.
CPC ...... *A61M 5/16831* (2013.01); *A61M 5/1456* (2013.01); *A61B 5/4839* (2013.01);
(Continued)

(58) Field of Classification Search
CPC .......... A61M 5/16854; A61M 5/16831; A61M 2005/16863; A61M 2005/16868; A61M 2005/16872
See application file for complete search history.

(56) References Cited

U.S. PATENT DOCUMENTS 3,630,417 A    12/1971    De Haas
4,185,759 A    1/1980    Zissimopoulos
(Continued)

FOREIGN PATENT DOCUMENTS

CN    101371127 A    2/2009
CN    102114282 A    7/2011
(Continued)

OTHER PUBLICATIONS

International Search Report dated Aug. 28, 2013 for PCT/US2013/042388 filed May 23, 2013, 4 pages.
(Continued)

*Primary Examiner* — Aarti B Berdichevsky
(74) *Attorney, Agent, or Firm* — Patterson Thuente Pedersen, P.A.

(57) ABSTRACT

A system for occlusion detection could include a syringe pump for a syringe containing a medication, wherein the syringe includes a plunger and the syringe pump includes a plunger driver. A bendable element could be integrally formed with the plunger driver, and a force sensor could also be integrally formed with the plunger driver. Upon occurrence of an occlusion, the plunger would exert a force backwardly against the bendable element, thereby deflecting the bendable element into contact with the force sensor to thereby generate a signal indicating the occurrence of the occlusion.

6 Claims, 4 Drawing Sheets

(52) U.S. Cl.
CPC ............... *A61B 2560/0266* (2013.01); *A61M 2005/16863* (2013.01); *A61M 2205/18* (2013.01); *A61M 2205/332* (2013.01); *A61M 2205/50* (2013.01)

(56) References Cited

U.S. PATENT DOCUMENTS

| | | |
|---|---|---|
| 4,236,880 A | 12/1980 | Archibald |
| 4,336,800 A | 6/1982 | Pastrone |
| 4,544,369 A | 10/1985 | Skakoon et al. |
| 4,747,828 A | 5/1988 | Tseo |
| 4,762,518 A | 8/1988 | Kreinick |
| 4,804,368 A | 2/1989 | Skakoon et al. |
| 4,976,151 A | 12/1990 | Morishita |
| 4,978,335 A | 12/1990 | Arthur, III |
| 5,034,004 A | 7/1991 | Crankshaw |
| 5,232,449 A | 8/1993 | Stern et al. |
| 5,295,967 A | 3/1994 | Rondelet et al. |
| 5,395,320 A | 3/1995 | Padda et al. |
| 5,399,171 A | 3/1995 | Bowman et al. |
| 5,501,665 A | 3/1996 | Jhuboo et al. |
| 5,647,853 A | 7/1997 | Feldmann et al. |
| 5,814,015 A * | 9/1998 | Gargano ............. A61M 5/1456 604/151 |
| 5,989,222 A | 11/1999 | Cole et al. |
| 7,150,724 B2 * | 12/2006 | Morris ................. A61M 5/1456 604/131 |
| 2002/0045861 A1 | 4/2002 | Tribe |
| 2002/0077852 A1 | 6/2002 | Ford et al. |
| 2003/0069559 A1 | 4/2003 | Platt et al. |
| 2003/0205587 A1 | 11/2003 | Tribe et al. |
| 2003/0229311 A1 | 12/2003 | Morris et al. |
| 2003/0233069 A1 | 12/2003 | Gillespie et al. |
| 2004/0073161 A1 | 4/2004 | Tachibana |
| 2005/0096593 A1 | 5/2005 | Pope et al. |
| 2005/0234387 A1 | 10/2005 | Tonelli et al. |
| 2007/0244469 A1 | 10/2007 | Ozeri et al. |
| 2010/0214110 A1 | 8/2010 | Wang et al. |
| 2010/0262078 A1 | 10/2010 | Blomquist |

FOREIGN PATENT DOCUMENTS

| | | |
|---|---|---|
| JP | S59-97671 | 6/1984 |
| JP | 06-190036 A | 7/1994 |
| JP | 2008-264140 A | 11/2008 |
| WO | WO 2009/113341 A1 | 9/2009 |
| WO | WO 2011009224 A2 | 1/2011 |
| WO | WO 2011/093103 A1 | 8/2011 |

OTHER PUBLICATIONS

European Search Report, EP Application No. EP13794119, completed Oct. 13, 2015, 7 pages.
PCT Notification Concerning Transmittal of International Preliminary Report on Patentability, International Preliminary Report on Patentability, and Written Opinion of the International Searching Authority, Cited in PCT/US2013/042388, dated Dec. 4, 2014, 8 pgs.
Chinese Office Action, Application No. 201380027501.2, dated Mar. 1, 2016, 7 pages.
Patent Examination Report No. 1, for Australian Application No. 2013266278, dated Oct. 15, 2016, 2 pages.
Office Action dated Mar. 1, 2017 for Japanese Application No. 2015-514175, 8 pages.
Office Action dated Feb. 6, 2018 for Japanese Application No. 2015-514175, 12 pages.

* cited by examiner

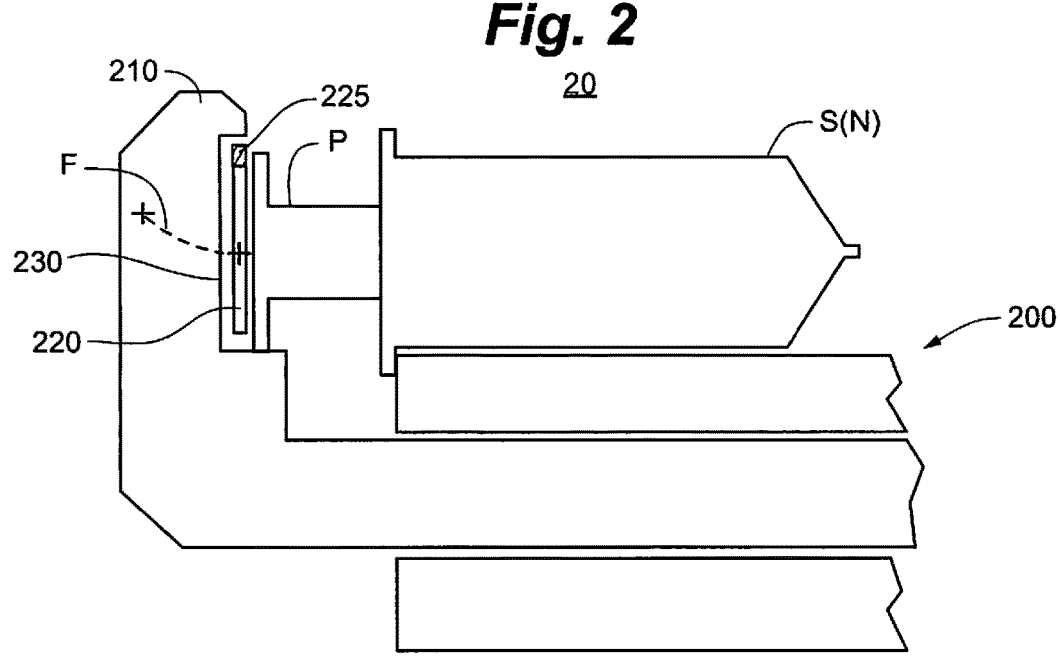
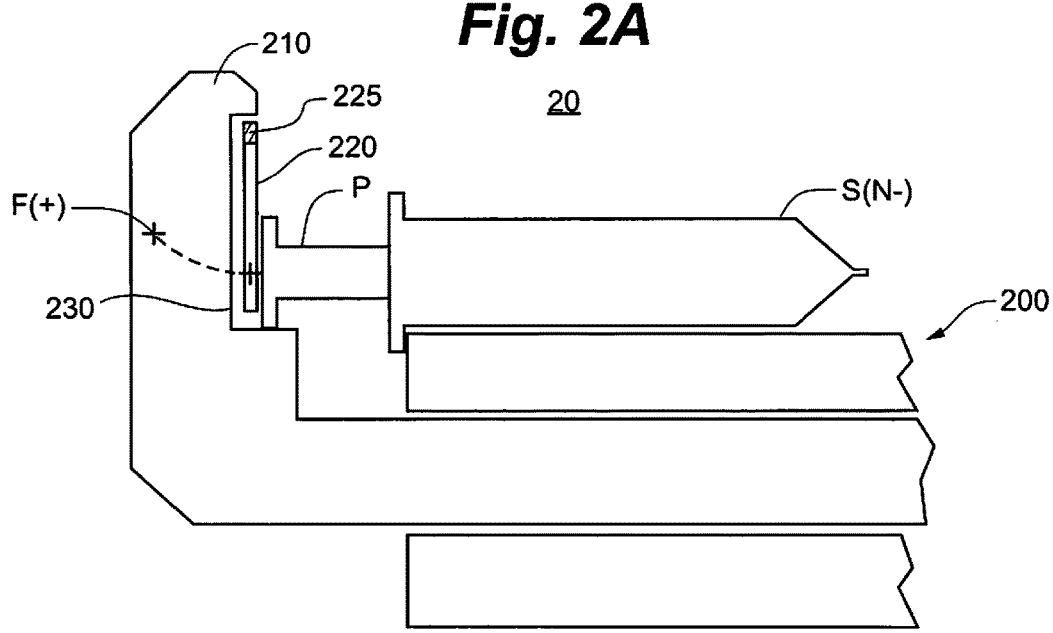

OCCLUSION DETECTION

RELATED APPLICATIONS

The present application is a National Phase entry of PCT Application No. PCT/US2013/042388, filed May 23, 2013, which claims priority from U.S. Provisional Patent. Application No. 61/651.860, filed May 25, 2012, said applications being hereby incorporated by reference herein in their entirety.

TECHNICAL FIELD

This disclosure relates generally to medical devices. More particularly, this disclosure relates to systems for, and methods of, occlusion detection.

BACKGROUND

In the medical arts, the term "occlusion" typically refers to the blocking or restriction of a normally open passage. In some instances, an occlusion is desired such as when a catheter is pinched off or temporarily collapsed into a closed state intentionally by a practitioner during a medical procedure. In other instances, an unintended occlusion could result in a potentially dangerous situation. For example, in the field of medication delivery devices and systems including so-called "syringe pumps", typically a pre-filled medication syringe is mechanically driven under microprocessor control to deliver a prescribed dose of medication at a controlled rate to a patient through an infusion line fluidly connected to the syringe. Syringe pumps typically include a motor that rotates a leadscrew. The leadscrew in turn activates a plunger driver which forwardly pushes a plunger within a barrel of the syringe. Pushing the plunger forward thus forces the dose of medication outwardly from the syringe, into the infusion line, and to the patient intravenously. Examples of syringe pumps are disclosed in, for example, U.S. Pat. No. 4,978,335 titled "Infusion Pump with Bar Code Input to Computer" and U.S. Pat. Applic. Pub. No. 2005/0096593 titled "Syringe Pump Rapid Occlusion Detection System". As used throughout this disclosure, the term "syringe pump" is intended to generally pertain to any device which acts on a syringe to controllably force fluid outwardly therefrom.

In such devices, an occlusion might occur when the intended and commanded forward progression of the plunger longitudinally through the syringe barrel is blocked or otherwise impeded, as when for example the infusion line tubing is kinked or otherwise structurally blocked to some degree. If the occlusion is not noticed, the patient likely would not receive the prescribed medication leading to potentially serious consequences.

Attempts to sense or detect occlusions in medical devices such as syringe pumps have therefore been made. For example, some syringe pumps detect occlusions by use of a pressure sensor that senses a force exerted by the aforementioned syringe thumb-press on the plunger driver. When the force experienced by the pressure sensor exceeds a predetermined threshold force, a processor connected to the pressure sensor generates a signal indicating that an occlusion has possibly occurred or is possibly occurring. Since syringe pumps are typically capable of accommodating a range of syringe diameters or sizes (e.g., 10 ml through 50 ml capacities) the plunger driver and pressure sensor may likely experience varying occlusion force vectors depending upon which particular size of syringe is being used in the syringe pump, leading to varying accuracy and responsiveness overall in the pump's occlusion sensing system. Since the occlusion force (F) is a function of pressure (P) exerted on the sensor over an area (A) experiencing the pressure (i.e., $P=F/A$) as the area decreases the pressure increases. Typically, therefore, smaller diameter syringes yield smaller sensed forces for given pressures upon occurrences of occlusions. Thus, known occlusion detection systems and methods have not been entirely satisfactory in sensing and signaling occlusions for relatively smaller diameter syringes.

Consequently, it would be useful and advantageous to provide systems for, and methods of, occlusion detection, particularly when using syringes of relatively small diameters in syringe pumps.

SUMMARY

This disclosure describes novel and inventive systems for, and methods of, occlusion detection.

In one aspect, a system for occlusion detection could include a syringe pump for a syringe containing a medication, wherein the syringe includes a plunger and the syringe pump includes a plunger driver. A bendable element could be integrally formed with the plunger driver, and a force sensor could also be integrally formed with the plunger driver. Upon occurrence of an occlusion, the plunger would exert a force backwardly against the bendable element, thereby deflecting the bendable element into contact with the force sensor to thereby generate a signal indicating the occurrence of the occlusion.

In another aspect, a system of occlusion detection could include a syringe pump for a syringe containing a medication, wherein the syringe includes a plunger and the syringe pump includes a plunger driver. A pivotable element could be connected to the plunger driver by a link A force sensor could be integrally formed with the plunger driver. Upon occurrence of an occlusion, the plunger would exert a force backwardly against the pivotable element, thereby deflecting the pivotable element about the link into contact with the force sensor to thereby generate a signal indicating the occurrence of the occlusion.

In another aspect, a system of occlusion detection could include a syringe pump for a syringe containing a medication, wherein the syringe includes a plunger and the syringe pump includes a plunger driver. A pivotable sliding element having a spring-loaded slot could be connected to the plunger driver by a link residing within the spring-loaded slot. A force sensor could be integrally formed with the plunger driver. Upon occurrence of an occlusion, the plunger would exert a force backwardly against the pivotable sliding element, thereby deflecting the pivotable sliding element about the link into contact with the force sensor to thereby generate a signal indicating the occurrence of the occlusion.

In another aspect, a system of occlusion detection could include a syringe pump for a syringe containing a medication, wherein the syringe includes a plunger and the syringe pump includes a plunger driver. A substantially unitary, combination component of a bendable element with a force sensor could be integrally formed with the plunger driver. Upon occurrence of an occlusion, the plunger would exert a force backwardly against the combination component, thereby deflecting the combination component such that a signal is thereby generated to indicate the occurrence of the occlusion.

In another aspect, a system for occlusion detection could include a syringe pump for a syringe containing a medication, wherein the syringe includes a plunger and the syringe pump includes a plunger driver. A bendable element could be integrally formed with the plunger driver, and a force sensor could also be integrally formed with the plunger driver. Upon occurrence of an occlusion, the plunger would exert a force backwardly against the bendable element, thereby deflecting the bendable element into contact with the force sensor to thereby generate a signal indicating the occurrence of the occlusion. The system for occlusion detection could be characterised in that forces exerted backwardly against the bendable element resulting from occurrences of occlusions, acting on the force sensor, increase in magnitude as syringe sizes decrease due to correspondingly greater moment arms on the bendable element.

In another aspect, a system of occlusion detection could include a syringe pump for a syringe containing a medication, wherein the syringe includes a plunger and the syringe pump includes a plunger driver. A pivotable element could be connected to the plunger driver by a link. A force sensor could be integrally formed with the plunger driver. Upon occurrence of an occlusion, the plunger would exert a force backwardly against the pivotable element, thereby deflecting the pivotable element about the link into contact with the force sensor to thereby generate a signal indicating the occurrence of the occlusion. The system of occlusion detection could be characterised in that forces exerted backwardly against the pivotable element resulting from occurrences of occlusions, acting on the force sensor, increase in magnitude as syringe sizes decrease due to correspondingly greater moment arms on the pivotable element.

In another aspect, a system of occlusion detection could include a syringe pump for a syringe containing a medication, wherein the syringe includes a plunger and the syringe pump includes a plunger driver. A pivotable sliding element having a spring-loaded slot could be connected to the plunger driver by a link residing within the spring-loaded slot. A force sensor could be integrally formed with the plunger driver. Upon occurrence of an occlusion, the plunger would exert a force backwardly against the pivotable sliding element, thereby deflecting the pivotable sliding element about the link into contact with the force sensor to thereby generate a signal indicating the occurrence of the occlusion. The system of occlusion detection could be characterised in that forces exerted backwardly against the pivotable sliding element resulting from occurrences of occlusions, acting on the force sensor, increase in magnitude as syringe sizes decrease due to correspondingly greater moment arms on the pivotable sliding element.

In another aspect, a system of occlusion detection could include a syringe pump for a syringe containing a medication, wherein the syringe includes a plunger and the syringe pump includes a plunger driver. A substantially unitary, combination component of a bendable element with a force sensor could be integrally formed with the plunger driver. Upon occurrence of an occlusion, the plunger would exert a force backwardly against the combination component, thereby deflecting the combination component such that a signal is thereby generated to indicate the occurrence of the occlusion. The system for occlusion detection could be characterised in that forces exerted backwardly against the combination component resulting from occurrences of occlusions, acting on the combination component, increase in magnitude as syringe sizes decrease due to correspondingly greater moment arms on the combination component.

In another aspect, a method of occlusion detection could include providing a syringe pump for a syringe containing a medication, wherein the syringe includes a plunger and the syringe pump includes (i) a plunger driver, (ii) an element with the plunger driver, the element being selected from a group consisting of a bendable element, a pivotable element, and a pivotable sliding element, and (iii) a force sensor integrally formed with the plunger driver. Upon occurrence of an occlusion, the plunger would exert a force backwardly against the element, thereby deflecting the element into contact with the force sensor to thereby generate a signal indicating the occurrence of the occlusion. The medication could be administered to a patient by way of the syringe pump, and the signal generated by the sensor could be sent to medical staff upon the occurrence of the occlusion.

In another aspect, a method of occlusion detection could include providing a syringe pump for a syringe containing a medication, wherein the syringe includes a plunger and the syringe pump includes (i) a plunger driver and (ii) a substantially unitary, combination component of a bendable element with a force sensor, with the plunger driver. Upon occurrence of an occlusion, the plunger would exert a force backwardly against the combination component, thereby deflecting the combination component such that a signal is thereby generated to indicate the occurrence of the occlusion. The medication could be administered to a patient by way of the syringe pump, and the signal generated by the sensor could be sent to medical staff upon the occurrence of the occlusion.

BRIEF DESCRIPTION OF THE DRAWINGS

Systems for, and methods of, occlusion detection are illustrated by way of example and not limitation in the figures of the accompanying drawings in which:

FIG. 2 is a schematic diagram of an alternative embodiment of a system for occlusion detection, in use with a relatively large medication syringe.

FIG. 2A is schematic diagram of the system shown in FIG. 2, in use with a relatively small medication syringe.

DETAILED DESCRIPTION

Occlusion detection systems and methods, that are described in greater detail by way of examples herein, make novel and inventive use of decreasing syringe diameters or sizes in syringe pumps to compensate for the aforementioned relatively smaller sensed occlusion forces that are otherwise generated by smaller diameter syringes. Such compensation advantageously results in more constant occlusion forces sensed for given pressures across varying ranges of syringe diameters or sizes used in syringe pumps; and better resolution and sensitivity in occlusion detection is achieved for smaller syringes that are used in, for example, neonatal care units when accuracy and precision in medication delivery are of paramount importance.

Generally, the aforementioned compensation is achieved by way of an element with a plunger driver of a syringe pump that is mechanically linked to a plunger of a syringe in the pump. The element is capable of bending, pivoting, or rotating about a point, upon displacement by an occlusion force acting backwardly on it as transmitted by the plunger. The element then bends, pivots, or rotates about the point, and thereby applies a force to a force sensor. The force sensor then outputs a signal indicative of an occurrence of an occlusion. As syringe diameter decreases, such as when, e.g., a 30 ml syringe is replaced in the pump by a 20 ml syringe, an occlusion force from the plunger of the smaller syringe acts on the element more distantly from the point about which the element bends, pivots, or rotates; and thus a relatively larger moment arm results with a correspondingly higher force experienced by the force sensor.

Figure 1:
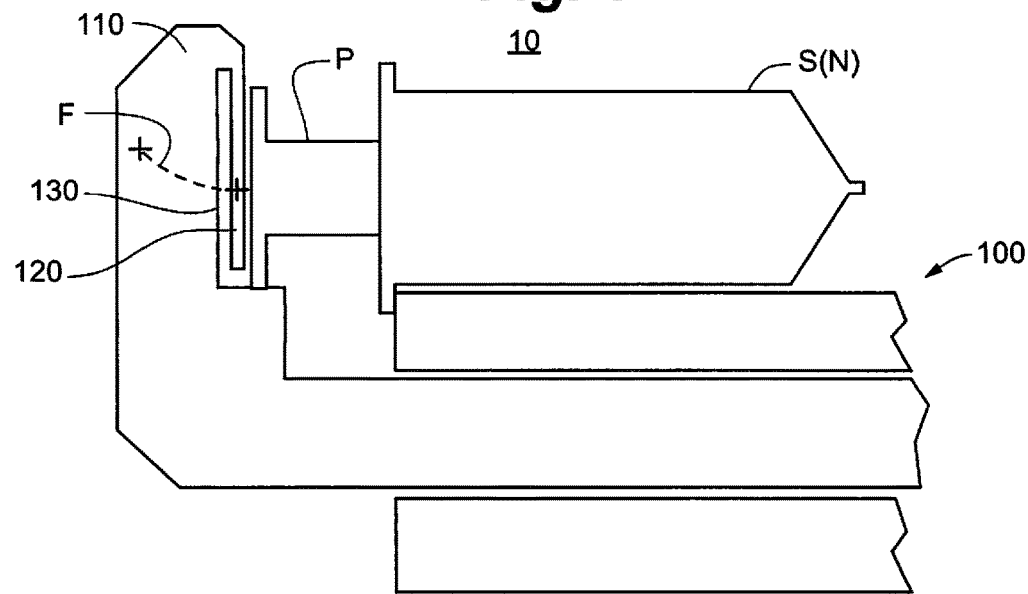
FIG. 1 is a schematic diagram of a system for occlusion detection, in use with a relatively large medication syringe.
Figure 1A:
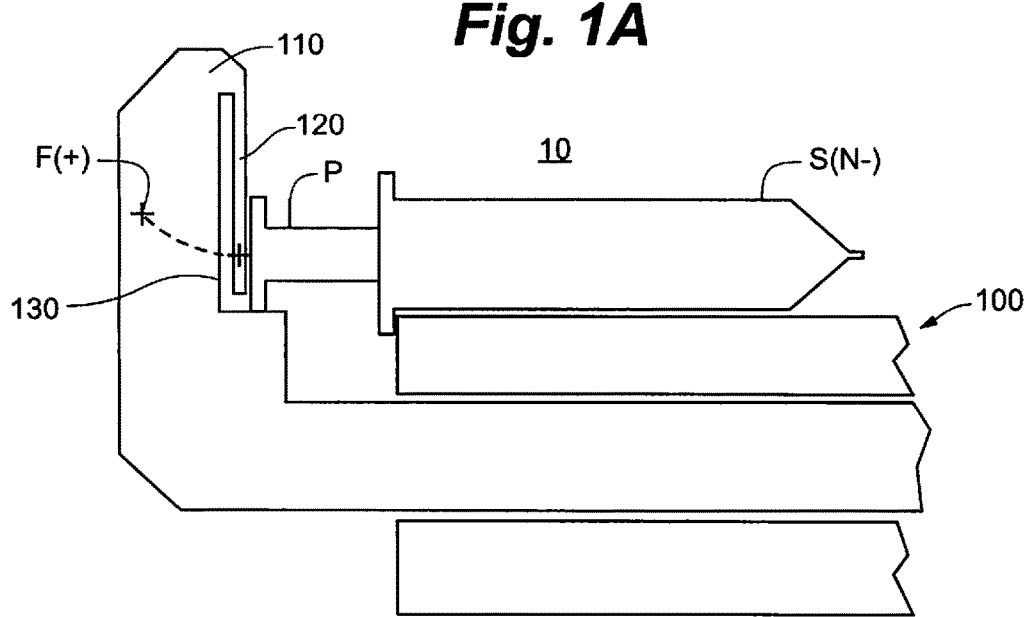
FIG. 1A is schematic diagram of the system shown in FIG. 1, in use with a relatively small medication syringe.

Referring now to FIG. 1, therein illustrated generally is an example of an embodiment of a system for occlusion detection 10. System 10 includes a syringe pump 100 for a syringe S having a plunger P. Syringe S is of a size or diameter (N) (e.g., a 30 ml syringe) that contains a medication to be delivered to a patient from pump 100 acting on syringe S by way of a plunger driver 110. Driver 110 includes an integrally formed bendable element 120. A force sensor 130 is also integrally formed with driver 110. As shown in FIG. 1, upon occurrence of an occlusion plunger P would exert a force backwardly against bendable element 120, thereby deflecting element 120 (indicated by phantom line F) into contact with force sensor 130 to thereby generate a signal indicating the occurrence of the occlusion. With reference now to FIG. 1A, it is to be appreciated and understood that upon occurrence of an occlusion with use of a syringe S of a size, or diameter, (N−) (e.g., a 20 ml syringe) plunger P would exert a force backwardly against bendable element 120, but at a greater distance downwardly along element 120 compared to FIG. 1. Thereby, in FIG. 1A, element 120 would be deflected (indicated by phantom line F(+)) with a greater moment arm and thus into more forceful contact with force sensor 130, compared to such contact from a relatively shorter moment arm shown in FIG. 1 from the larger syringe size (N).

Another embodiment of an example of a system for occlusion detection 20 is illustrated generally in FIG. 2. System 20 includes a syringe pump 200 for a syringe S having a plunger P. Syringe S is of a size or diameter (N) (e.g., a 30 ml syringe) that contains a medication to be delivered to a patient from pump 200 acting on syringe S by way of a plunger driver 210. A pivotable element 220 is connected to driver 210 by a link 225 (e.g., a pin through a corresponding hole in element 220). A force sensor 230 is integrally formed with driver 210. As shown in FIG. 1, upon occurrence of an occlusion plunger P would exert a force backwardly against pivotable element 220, thereby deflecting element 220 about link 225 (indicated by phantom line F) into contact with force sensor 230 to thereby generate a signal indicating the occurrence of the occlusion. With reference now to FIG. 2A, it is to be appreciated and understood that upon occurrence of an occlusion with use of a syringe S of a size or diameter (N−) (e.g., a 20 ml syringe) plunger P would exert a force backwardly against pivotable element 220, but at a greater distance downwardly along element 220 compared to FIG. 2. Thereby, in FIG. 2A, element 220 would be deflected (indicated by phantom line F(+)) with a greater moment arm and thus into more forceful contact with force sensor 230, compared to such contact from a relatively shorter moment arm shown in FIG. 2 from the larger syringe size (N).

Figure 3:
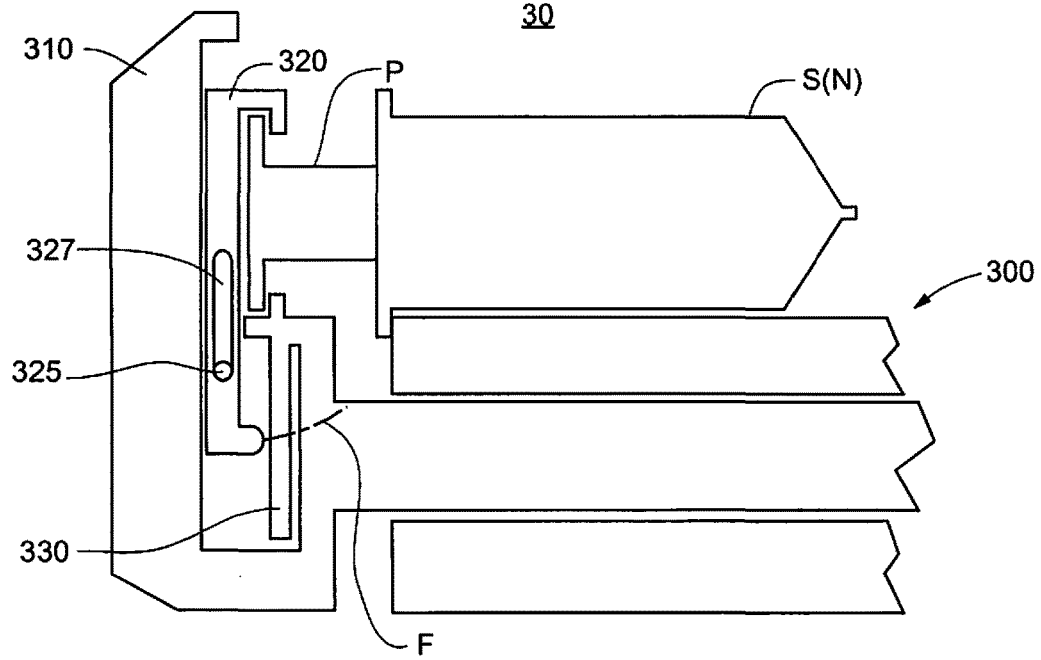
FIG. 3 is a schematic diagram of an alternative embodiment of a system for occlusion detection, in use with a relatively large medication syringe.
Figure 3A:
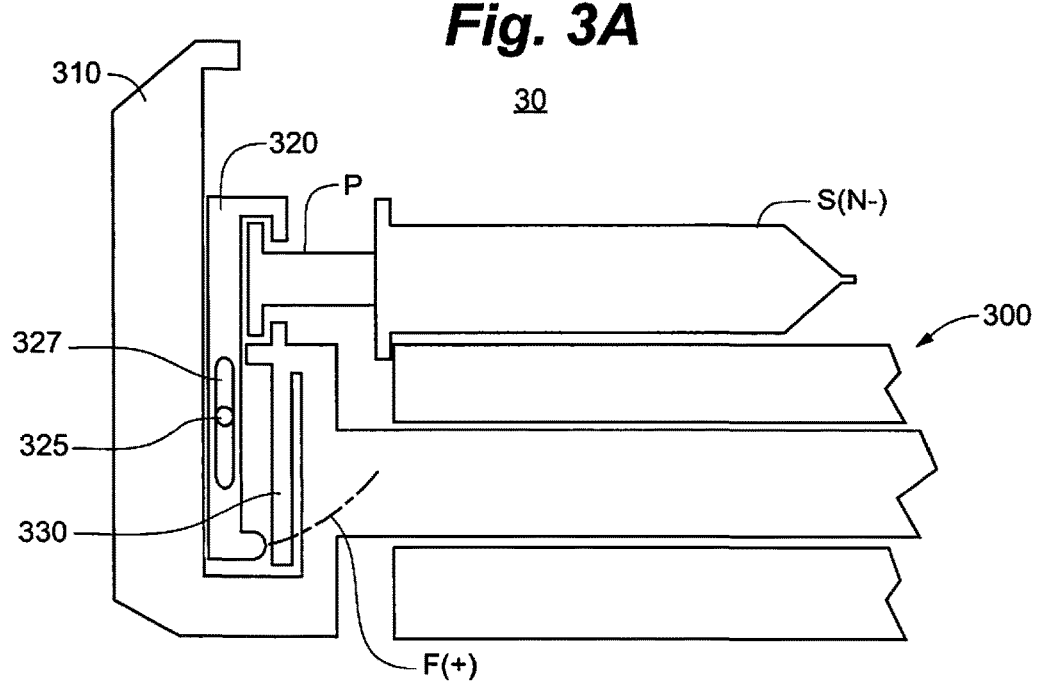
FIG. 3A is schematic diagram of the system shown in FIG. 3, in use with a relatively small medication syringe.

Another embodiment of an example of a system for occlusion detection 30 is illustrated generally in FIG. 3. System 30 includes a syringe pump 300 for a syringe S having a plunger P. Syringe S is of a size or diameter (N) (e.g., a 30 ml syringe) that contains a medication to be delivered to a patient from pump 300 acting on syringe S by way of a plunger driver 310. A pivotable sliding element 320 is connected to driver 310 by a link 325 (e.g., a pin in a spring-loaded slot 327 in element 320; details of the spring-loaded slot 327 have been omitted for clarity of the drawing). A force sensor 330 is integrally formed with driver 310. As shown in FIG. 3, upon occurrence of an occlusion plunger P would exert a force backwardly against pivotable sliding element 320, thereby deflecting element 320 about link 325 (indicated by phantom line F) into contact with force sensor 330 to thereby generate a signal indicating the occurrence of the occlusion. With reference now to FIG. 3A, it is to be appreciated and understood that upon occurrence of an occlusion with use of a syringe S of a size or diameter (N−) (e.g., a 20 ml syringe) plunger P would exert a force backwardly against pivotable sliding element 320, but at a greater distance downwardly along element 320 compared to FIG. 3. Thereby, in FIG. 3A, element 320 would be deflected (indicated by phantom line F(+)) with a greater moment arm and thus into more forceful contact with force sensor 330, compared to such contact from a relatively shorter moment arm shown in FIG. 3 from the larger syringe size (N).

Figure 4:
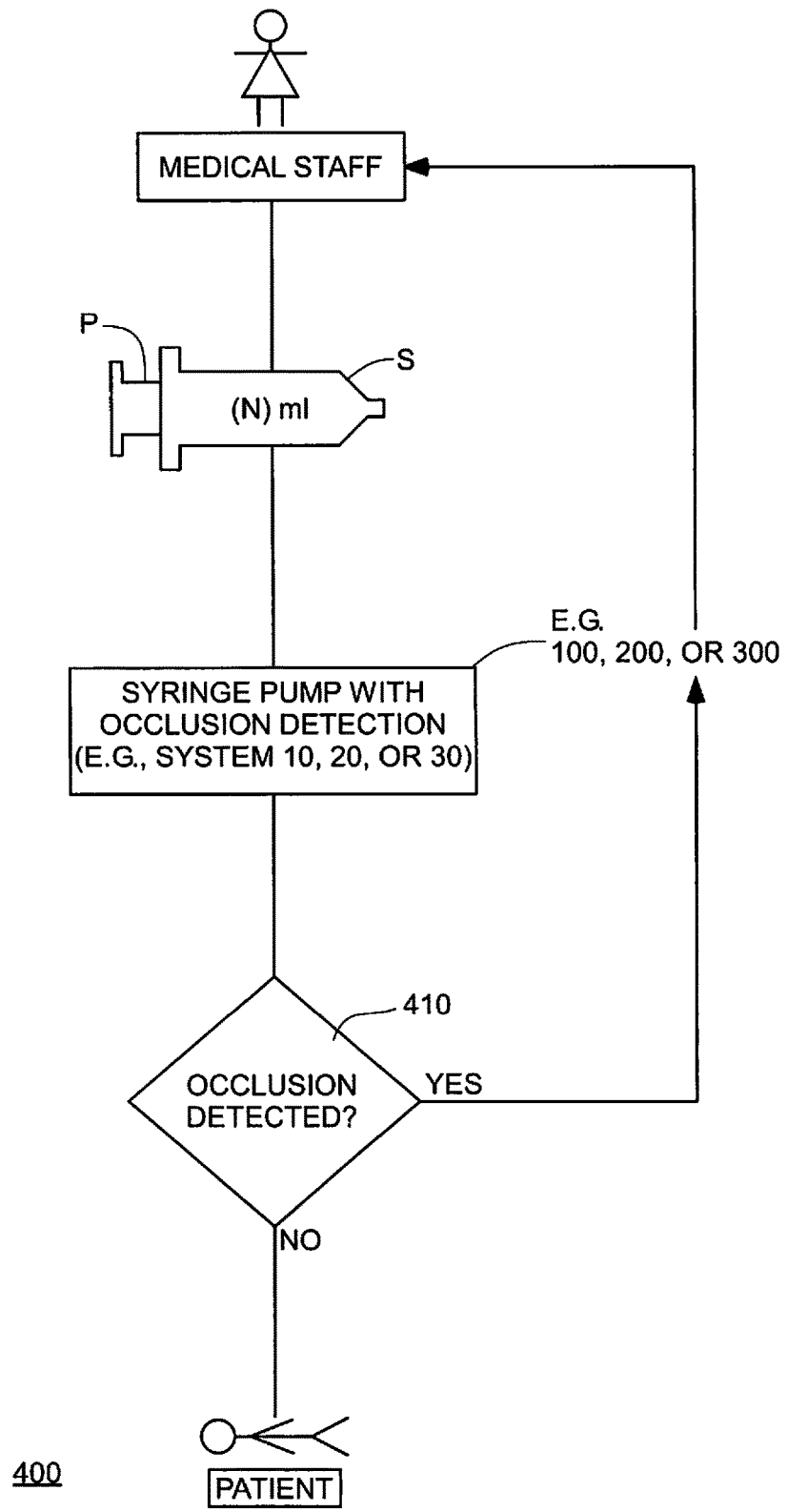
FIG. 4 is a schematic block diagram of a method for occlusion detection.

Referring now to FIG. 4, therein illustrated generally is an example of a method for occlusion detection 400 in, e.g., a clinical setting having medical staff M. In this example, medical staff M would load a syringe S of a size (N) containing a selected medication for a patient into a syringe pump (e.g., the aforementioned pumps 100, 200, or 300). As described by example above, syringe S would include a plunger P. The syringe pump would include a plunger driver such as, e.g., the aforementioned drivers 110, 210, and 310. An element (e.g., the aforementioned bendable element 120, pivotable element 220, or pivotable sliding element 320) would be included with the plunger driver. A force sensor such as, e.g., the aforementioned sensors 130, 230, or 330, would be integrally formed with the plunger driver. The syringe pump would administer the medication to the patient (typically, e.g., through an intravenous line from the syringe to the patient). Upon occurrence of an occlusion, the plunger would exert a force backwardly against the element, thereby deflecting the element into contact with the force sensor. The force sensor would responsively generate a signal that would be sent to the medical staff alerting them to the occurrence of the occlusion as indicated by symbol 410 in the drawing.

Although not illustrated herein, another embodiment of an example of a system for occlusion detection could utilize a substantially unitary, combination component of a bendable element with a force sensor. I.e., the force sensor would respond to a bending moment by being incorporated with or into the bendable element itself, instead of separate bendable element and force sensor components as shown in, e.g., the various examples of FIGS. 1, 2, and 3. In embodiments that have a substantially unitary, combination component of a bendable element with a force sensor—instead of separate components—a smaller syringe in the pump would, upon occurrence of an occlusion, apply a force closer to a free end of the combination component which would again, in turn, advantageously result in a greater moment arm and correspondingly higher force sensor output.

Regardless of particular components or modes of action, it is to be appreciated and understood that systems for, and methods of, occlusion detection such as have been described by example or otherwise contemplated herein could detect occlusions to enhance the safety and accuracy of delivery of medication from syringes to patients. As aforementioned, novel and inventive use is made of decreasing syringe diameters or sizes to compensate for the aforementioned otherwise relatively smaller sensed occlusion forces generated by smaller diameter syringes. That is, what heretofore had been a disadvantage in occlusion detection—decreasing syringe diameters or sizes—is now used to technical advantage as aforedescribed, which may, for example, quite advantageously permit faster occlusion detection in small syringes.

It is also to be particularly appreciated and understood that any embodiment of systems for, and methods of, occlusion detection that have been described by example or otherwise contemplated herein could advantageously be used, or function in association, with principles of determining discrete force values. Such discrete force values could, in turn, determine whether relationships between them depart from expected relationships, etc., as disclosed in the aforecited U.S. Pat. Applic. Pub. No. 2005/0096593; and an entirety of that Pub. No. 2005/0096593 is incorporated herein by reference thereto.

While systems for, and methods of, occlusion detection have been particularly shown and described with reference to the accompanying figures and specification, it should be understood however that other modifications thereto are of course possible; and all of them are intended to be within the true spirit and scope of novel and inventive systems and methods described herein. Thus, configurations and designs of various features could be modified or altered depending upon particular embodiments.

Additionally, dimensioning and scaling of the drawings herein have been chosen to clearly show details of example embodiments. Thus, in some embodiments it is possible that spacing between various features might be visually imperceptible—e.g., the bendable, pivotable, and pivotable sliding elements; and the plunger driver. In any event, dimensioning and scaling could vary significantly across various embodiments of occlusion detection systems and methods.

It should also be appreciated that types, components, dimensions, fabrication processes, and other particulars and parameters of aforedescribed example embodiments may be substituted for others as desired, or that accessories may be added thereto. For example, in one embodiment, the force sensor could comprise a commercially available Honeywell 1865 Pressure Transducer.

It is also to be understood in general that any suitable alternatives may be employed to provide novel and inventive systems for, and methods of, occlusion detection described by example or otherwise contemplated herein. As such, although the bendable elements, force sensors, and combination components (collectively, regardless of particular constructions, "force components") described by example herein have been further described as being "integrally formed" with plunger drivers, it is to be appreciated and understood that this "integrally formed" terminology broadly includes constructions wherein (i) the force components are formed essentially as one with the plunger driver and also wherein (ii) the force components are physically separate from but attached to, connected to, or otherwise contained within, the plunger driver.

Lastly, compositions, sizes, and strengths of various aforementioned components of systems for, and methods of, occlusion detection described by example or otherwise contemplated herein are all a matter of design choice depending upon intended uses thereof.

Accordingly, these and other various changes or modifications in form and detail may also be made, without departing from the true spirit and scope of systems for, and methods of, occlusion detection that may be defined by the appended claims.

The invention claimed is:

1. A system for occlusion detection, comprising:
a syringe pump capable of accommodating a range of syringe diameters, said syringe pump including a plunger driver configured to apply a force to forwardly push a plunger within a barrel of a syringe loaded into said syringe pump;
a bendable element integrally formed with said plunger driver, said bendable element defining a moment arm between a bending point and a center of said force applied to said plunger, wherein said moment arm correspondingly increases with a decrease in a diameter of said syringe; and
a force sensor integrally formed with said plunger driver, wherein upon occurrence of an occlusion, said plunger exerts a force backwardly against said bendable element, thereby deflecting said bendable element into contact with said force sensor to thereby generate a signal indicating the occurrence of the occlusion, and wherein a force applied to said force sensor remains acceptable for proper detection and operation of the sensor when a syringe having a relatively small diameter is loaded into said syringe pump, due to occurrence of a correspondingly greater moment arm on said bendable element that is attributable to the relatively small diameter of the syringe.

2. The system for occlusion detection of claim 1 characterized in that forces exerted backwardly against said bendable element resulting from occurrences of occlusions, acting on said force sensor, increase in magnitude as syringe sizes decrease due to correspondingly greater moment arms on said bendable element.

3. A system for occlusion detection, comprising:
a syringe pump capable of accommodating a range of syringe diameters, said syringe pump including a plunger driver configured to apply a force to forwardly push a plunger within a barrel of a syringe loaded into said syringe pump; and
a substantially unitary, combination component of a bendable element with a force sensor, being integrally formed with said plunger driver, said bendable element defining a moment arm between a bending point and a center of said force applied to said plunger, wherein said moment arm correspondingly increases with a decrease in a diameter of said syringe, wherein upon occurrence of an occlusion, said plunger exerts a force backwardly against said combination component, thereby deflecting said combination component such that a signal is thereby generated to indicate the occurrence of the occlusion, and wherein a force applied to said force sensor remains acceptable for proper detection and operation of the sensor when a syringe having a relatively small diameter is loaded into said syringe pump, due to occurrence of a correspondingly greater moment arm on said bendable element that is attributable to the relatively small diameter of the syringe.

4. The system for occlusion detection of claim 3, characterized in that forces exerted backwardly against said combination component resulting from occurrences of occlusions, acting on said combination component, increase in magnitude as syringe sizes decrease due to correspondingly greater moment arms on said combination component.

5. A method of occlusion detection, comprising:
providing a syringe pump capable of accommodating a range of syringe diameters, said syringe pump including (i) a plunger driver configured to apply a force to forwardly push a plunger within a barrel of a syringe loaded into said syringe pump, (ii) an element with said plunger driver, said element being a bendable element defining a moment arm between a bending point and a center of said force applied to said plunger, wherein said moment arm correspondingly increases with a decrease in a diameter of said syringe, and (iii) a force sensor integrally formed with said plunger driver, wherein upon occurrence of an occlusion, said plunger exerts a force backwardly against said element, thereby deflecting said element into contact with said force sensor to thereby generate a signal indicating the occurrence of the occlusion, and wherein a force applied to said force sensor remains acceptable for proper detection and operation of the sensor when a syringe having a relatively small diameter is loaded into said syringe pump, due to occurrence of a correspondingly greater moment arm on said bendable element that is attributable to the relatively small diameter of the syringe;
administering the medication to a patient by way of said syringe pump; and
sending said signal generated by said sensor to medical staff, upon an occurrence of an occlusion.

6. A method of occlusion detection, comprising:
providing a syringe pump capable of accommodating a range of syringe diameters, said syringe pump including (i) a plunger driver configured to apply a force to forwardly push a plunger within a barrel of a syringe loaded into said syringe pump and (ii) a substantially unitary, combination component of a bendable element with a force sensor, with said plunger driver, said bendable element defining a moment arm between a bending point and a center of said force applied to said plunger, wherein said moment arm correspondingly increases with a decrease in a diameter of said syringe, wherein upon occurrence of an occlusion, the plunger exerts a force backwardly against said combination component, thereby deflecting said combination component such that a signal is thereby generated to indicate the occurrence of the occlusion, and wherein a force applied to said force sensor remains acceptable for proper detection and operation of the sensor when a syringe having a relatively small diameter is loaded into said syringe pump, due to occurrence of a correspondingly greater moment arm on said bendable element that is attributable to the relatively small diameter of the syringe;
administering the medication to a patient by way of said syringe pump; and
sending said signal generated by said combination component to medical staff, upon an occurrence of an occlusion.

* * * * *